(12) United States Patent
LaFontaine et al.

(10) Patent No.: US 7,004,175 B2
(45) Date of Patent: Feb. 28, 2006

(54) SYSTEM AND METHOD FOR PERCUTANEOUS CORONARY ARTERY BYPASS

(75) Inventors: Daniel M. LaFontaine, Plymouth, MN (US); Kent D. Harrison, Maple Grove, MN (US); Charles L. Euteneuer, St. Michael, MN (US); Roger N. Hastings, Maple Grove, MN (US); Lixiao Wang, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/436,863

(22) Filed: May 13, 2003

(65) Prior Publication Data

US 2003/0195457 A1   Oct. 16, 2003

Related U.S. Application Data

(60) Continuation of application No. 09/759,996, filed on Jan. 12, 2001, now Pat. No. 6,575,168, which is a continuation of application No. 09/391,112, filed on Sep. 7, 1999, now Pat. No. 6,253,769, which is a division of application No. 08/813,038, filed on Mar. 6, 1997, now Pat. No. 6,026,814.

(51) Int. Cl.
    *A61B 19/00*  (2006.01)
(52) U.S. Cl. ........................... 128/898; 623/1.1
(58) Field of Classification Search ............... 128/898
    See application file for complete search history.

(56) References Cited

U.S. PATENT DOCUMENTS 3,667,069 A    6/1972   Blackshear et al.
4,016,884 A    4/1977   Kwan-Gett
4,165,747 A    8/1979   Bermant
4,173,981 A   11/1979   Mortensen
4,190,909 A    3/1980   Ablaza
4,230,096 A   10/1980   Zeff et al.
4,368,736 A *  1/1983   Kaster ........................ 606/153
4,546,499 A   10/1985   Possis et al.
4,562,597 A    1/1986   Possis et al.
4,566,453 A    1/1986   Kumano et al.
4,601,718 A    7/1986   Possis et al.

(Continued)

FOREIGN PATENT DOCUMENTS

EP          0 769 272 A1     7/1997

(Continued)

OTHER PUBLICATIONS

Isner, Jeffrey M. et al., "The Current Status of Lasers in the Treatment of Cardiovascular Disease," *IEEE*, vol. QE-20, No. 12, Dec. 1984, pp. 1406-1420.

(Continued)

*Primary Examiner*—Thomas Barrett
(74) *Attorney, Agent, or Firm*—Crompton, Seager & Tufte, LLC

(57) ABSTRACT

A percutaneous system for bypassing a restriction in a native vessel of a mammal having an aorta includes providing a graft having a body portion with a first end, a second end and a lumen therebetween. An aperture is formed in the aorta. The graft is inserted into the aorta and the first end of the graft is connected to the aorta about the aperture in the aorta. An aperture is then formed in the native vessel distal of the restriction. The second end of the graft is connected to the native vessel about the aperture therein such that the lumen in the graft communicates with the aorta and the native vessel.

5 Claims, 12 Drawing Sheets

U.S. PATENT DOCUMENTS

| | | |
|---|---|---|
| 4,610,661 A | 9/1986 | Possis et al. |
| 4,667,673 A | 5/1987 | Li |
| 4,690,684 A | 9/1987 | McGreevy et al. |
| 4,710,192 A | 12/1987 | Liotta et al. |
| 4,721,109 A | 1/1988 | Healey |
| 4,790,819 A | 12/1988 | Li et al. |
| 4,803,984 A | 2/1989 | Narayanan et al. |
| 4,808,163 A | 2/1989 | Laub |
| 4,819,640 A | 4/1989 | Narayanan et al. |
| 4,827,931 A | 5/1989 | Longmore |
| 4,907,591 A | 3/1990 | Vasconcellos et al. |
| 4,911,164 A | 3/1990 | Roth |
| 4,995,857 A | 2/1991 | Arnold |
| 5,011,469 A | 4/1991 | Buckberg et al. |
| 5,037,428 A | 8/1991 | Picha |
| 5,047,039 A | 9/1991 | Avant et al. |
| 5,053,041 A | 10/1991 | Ansari et al. |
| 5,053,043 A | 10/1991 | Gottesman et al. |
| 5,061,245 A | 10/1991 | Waldvogel |
| 5,067,958 A | 11/1991 | Sandhaus |
| 5,080,663 A | 1/1992 | Mills et al. |
| 5,080,664 A | 1/1992 | Jain |
| 5,104,402 A | 4/1992 | Melbin |
| 5,122,154 A | 6/1992 | Rhodes |
| 5,144,961 A | 9/1992 | Chen et al. |
| 5,222,962 A | 6/1993 | Burkhart |
| 5,222,963 A | 6/1993 | Brinkerhoff et al. |
| 5,222,971 A | 6/1993 | Willard et al. |
| 5,234,445 A | 8/1993 | Walker et al. |
| 5,254,113 A | 10/1993 | Wilk |
| 5,281,236 A | 1/1994 | Bagnato et al. |
| 5,282,810 A | 2/1994 | Allen et al. |
| 5,287,861 A | 2/1994 | Wilk |
| 5,308,320 A | 5/1994 | Safar et al. |
| 5,314,436 A | 5/1994 | Wilk |
| 5,314,472 A | 5/1994 | Fontaine |
| 5,323,789 A | 6/1994 | Berggren et al. |
| 5,330,486 A | 7/1994 | Wilk |
| 5,364,389 A | 11/1994 | Anderson |
| 5,370,683 A | 12/1994 | Fontaine |
| 5,382,257 A | 1/1995 | Lewis et al. |
| 5,383,854 A | 1/1995 | Safar et al. |
| 5,383,928 A | 1/1995 | Scott et al. |
| 5,397,345 A | 3/1995 | Lazarus |
| 5,403,333 A | 4/1995 | Kaster et al. |
| 5,409,019 A | 4/1995 | Wilk |
| 5,425,705 A | 6/1995 | Evard et al. |
| 5,425,739 A | 6/1995 | Jessen |
| 5,429,144 A | 7/1995 | Wilk |
| 5,433,700 A | 7/1995 | Peters |
| 5,437,684 A | 8/1995 | Calabrese et al. |
| 5,441,507 A | 8/1995 | Wilk |
| 5,443,497 A | 8/1995 | Venbrux |
| 5,447,512 A | 9/1995 | Wilson et al. |
| 5,449,372 A | 9/1995 | Schmaltz et al. |
| 5,452,733 A | 9/1995 | Sterman et al. |
| 5,456,714 A | 10/1995 | Owen |
| 5,472,404 A | 12/1995 | Volgushev |
| 5,501,698 A | 3/1996 | Roth et al. |
| 5,522,884 A | 6/1996 | Wright |
| 5,527,319 A | 6/1996 | Green et al. |
| 5,527,324 A | 6/1996 | Krantz et al. |
| 5,536,251 A | 7/1996 | Evard et al. |
| 5,540,677 A | 7/1996 | Sinofsky |
| 5,540,701 A | 7/1996 | Sharkey et al. |
| 5,545,171 A | 8/1996 | Sharkey et al. |
| 5,554,162 A | 9/1996 | DeLange |
| 5,556,414 A | 9/1996 | Turi |
| 5,556,428 A | 9/1996 | Shah |
| RE35,352 E | 10/1996 | Peters |
| 5,562,728 A | 10/1996 | Lazarus et al. |
| 5,569,272 A | 10/1996 | Reed et al. |
| 5,569,274 A | 10/1996 | Rapacki et al. |
| 5,571,090 A | 11/1996 | Sherts |
| 5,571,215 A | 11/1996 | Sterman et al. |
| 5,584,803 A | 12/1996 | Stevens et al. |
| 5,588,949 A | 12/1996 | Taylor et al. |
| 5,591,179 A | 1/1997 | Edelstein |
| 5,591,212 A | 1/1997 | Keimel |
| 5,593,424 A | 1/1997 | Northrup III |
| RE35,459 E | 2/1997 | Junkman |
| 5,601,576 A | 2/1997 | Garrison |
| 5,601,581 A | 2/1997 | Fogarty et al. |
| 5,609,598 A | 3/1997 | Laufer et al. |
| 5,613,937 A | 3/1997 | Garrison et al. |
| 5,618,270 A | 4/1997 | Orejola |
| 5,643,292 A | 7/1997 | Hart |
| 5,653,744 A | 8/1997 | Khouri |
| 5,655,548 A | 8/1997 | Nelson |
| 5,662,124 A | 9/1997 | Wilk |
| 5,662,711 A | 9/1997 | Douglas |
| 5,676,670 A | 10/1997 | Kim |
| 5,682,906 A | 11/1997 | Sterman et al. |
| 5,685,857 A | 11/1997 | Negus et al. |
| 5,693,083 A | 12/1997 | Baker et al. |
| 5,702,368 A | 12/1997 | Stevens et al. |
| 5,702,412 A | 12/1997 | Popov et al. |
| 5,715,832 A | 2/1998 | Koblish et al. |
| 5,716,367 A | 2/1998 | Koike et al. |
| 5,718,725 A | 2/1998 | Sterman et al. |
| 5,722,426 A | 3/1998 | Kolff |
| 5,725,537 A | 3/1998 | Green et al. |
| 5,727,569 A | 3/1998 | Benetti et al. |
| 5,728,151 A | 3/1998 | Garrison et al. |
| 5,735,290 A | 4/1998 | Sterman et al. |
| 5,738,649 A | 4/1998 | Macoviak |
| 5,738,652 A | 4/1998 | Boyd et al. |
| 5,749,892 A | 5/1998 | Vierra et al. |
| 5,752,526 A | 5/1998 | Cosgrove |
| 5,755,682 A | 5/1998 | Knudson et al. |
| 5,755,687 A | 5/1998 | Donlon |
| 5,755,778 A | 5/1998 | Kleshinski |
| 5,758,663 A | 6/1998 | Wilk et al. |
| 5,766,151 A | 6/1998 | Valley et al. |
| 5,769,812 A | 6/1998 | Stevens et al. |
| 5,792,094 A | 8/1998 | Stevens et al. |
| 5,795,325 A | 8/1998 | Valley et al. |
| 5,797,920 A | 8/1998 | Kim |
| 5,797,933 A | 8/1998 | Snow et al. |
| 5,799,661 A | 9/1998 | Boyd et al. |
| 5,800,450 A | 9/1998 | Lary et al. |
| 5,800,552 A | 9/1998 | Forte |
| 5,836,311 A | 11/1998 | Borst et al. |
| 5,849,036 A | 12/1998 | Zarate |
| 5,855,210 A | 1/1999 | Sterman et al. |
| 5,855,614 A | 1/1999 | Stevens et al. |
| 5,868,770 A | 2/1999 | Rygaard |
| 5,893,369 A | 4/1999 | LeMole |
| 5,895,404 A | 4/1999 | Ruiz |
| 5,904,147 A | 5/1999 | Conlan et al. |
| 5,904,690 A | 5/1999 | Middleman et al. |
| 5,921,979 A | 7/1999 | Kovac et al. |
| 5,928,181 A | 7/1999 | Coleman et al. |
| 5,944,019 A | 8/1999 | Knudson et al. |
| 5,947,125 A | 9/1999 | Benetti |
| 5,947,919 A | 9/1999 | Krueger et al. |
| 5,976,178 A | 11/1999 | Goldsteen et al. |
| 6,026,814 A | 2/2000 | LaFontaine et al. |
| 6,035,856 A | 3/2000 | LaFontaine et al. |
| 6,155,264 A | 12/2000 | Ressemann et al. |
| 6,253,769 B1 | 7/2001 | LaFontaine et al. |
| 6,390,098 B1 | 5/2002 | LaFontaine et al. |
| 6,575,168 B1 | 6/2003 | LaFontaine et al. |

FOREIGN PATENT DOCUMENTS

| | | |
|---|---|---|
| JP | 97/281410 | 7/1997 |
| RU | 1600708 | 12/1995 |
| SU | 308752 | 7/1971 |
| SU | 388738 | 9/1971 |
| SU | 891076 | 12/1981 |
| SU | 1822750 A1 | 7/1982 |
| WO | WO 95/08364 | 3/1995 |
| WO | WO 95/10218 | 4/1995 |
| WO | WO 95/15192 | 6/1995 |
| WO | WO 95/16476 | 6/1995 |
| WO | WO 96/10375 | 4/1996 |
| WO | WO 96/17644 | 6/1996 |
| WO | WO 96/25886 | 8/1996 |
| WO | WO 96/30072 | 10/1996 |
| WO | WO 96/30073 | 10/1996 |
| WO | WO 96/32882 | 10/1996 |
| WO | WO 97/12555 | 4/1997 |
| WO | WO 97/13463 | 4/1997 |
| WO | WO 97/13468 | 4/1997 |
| WO | WO 97/13471 | 4/1997 |
| WO | WO 97/26939 | 7/1997 |
| WO | WO 97/37984 | 10/1997 |
| WO | WO 97/40751 | 11/1997 |
| WO | WO 98/06356 | 2/1998 |
| WO | WO 98/07399 | 2/1998 |
| WO | WO 98/10714 | 3/1998 |
| WO | WO 98/16161 | 4/1998 |
| WO | WO 98/16174 | 4/1998 |
| WO | WO 98/17182 | 4/1998 |
| WO | WO 98/17187 | 4/1998 |
| WO | WO 98/15237 | 5/1998 |
| WO | WO 98/19607 | 5/1998 |
| WO | WO 98/19634 | 5/1998 |
| WO | WO 98/19636 | 5/1998 |
| WO | WO 98/31302 | 7/1998 |
| WO | WO 98/32380 | 7/1998 |
| WO | WO 98/35626 | 8/1998 |
| WO | WO 98/37814 | 9/1998 |
| WO | WO 98/51223 | 11/1998 |
| WO | WO 98/52475 | 11/1998 |
| WO | WO 98/57590 | 12/1998 |
| WO | WO 98/57591 | 12/1998 |
| WO | WO 98/57592 | 12/1998 |
| WO | WO 99/04836 | 2/1999 |
| WO | WO 99/04845 | 2/1999 |
| WO | WO 99/17683 | 4/1999 |
| WO | WO 99/18887 | 4/1999 |
| WO | WO 99/35975 | 7/1999 |
| WO | WO 99/35977 | 7/1999 |
| WO | WO 99/35978 | 7/1999 |
| WO | WO 99/35979 | 7/1999 |
| WO | WO 99/35980 | 7/1999 |
| WO | WO 99/36000 | 7/1999 |
| WO | WO 99/36001 | 7/1999 |
| WO | WO 99/38459 | 8/1999 |
| WO | WO 99/40853 | 8/1999 |
| WO | WO 99/40868 | 8/1999 |

OTHER PUBLICATIONS

Monro, Ian et al., "The Possibility of Myocardial Revascularization by Creation of a Left Ventriculocoronary Artery Fistula," *Journal of Thoracic and Cardiovascular Surgery*, vol. 58, No. 1, Jul. 1969, pp. 25-32.

* cited by examiner

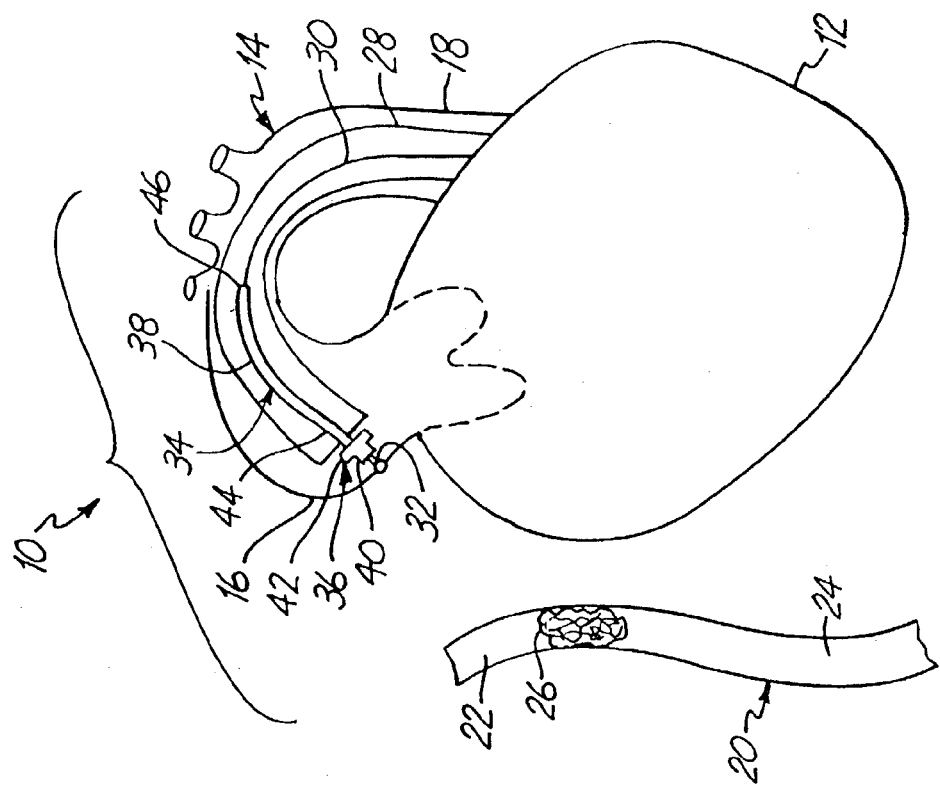
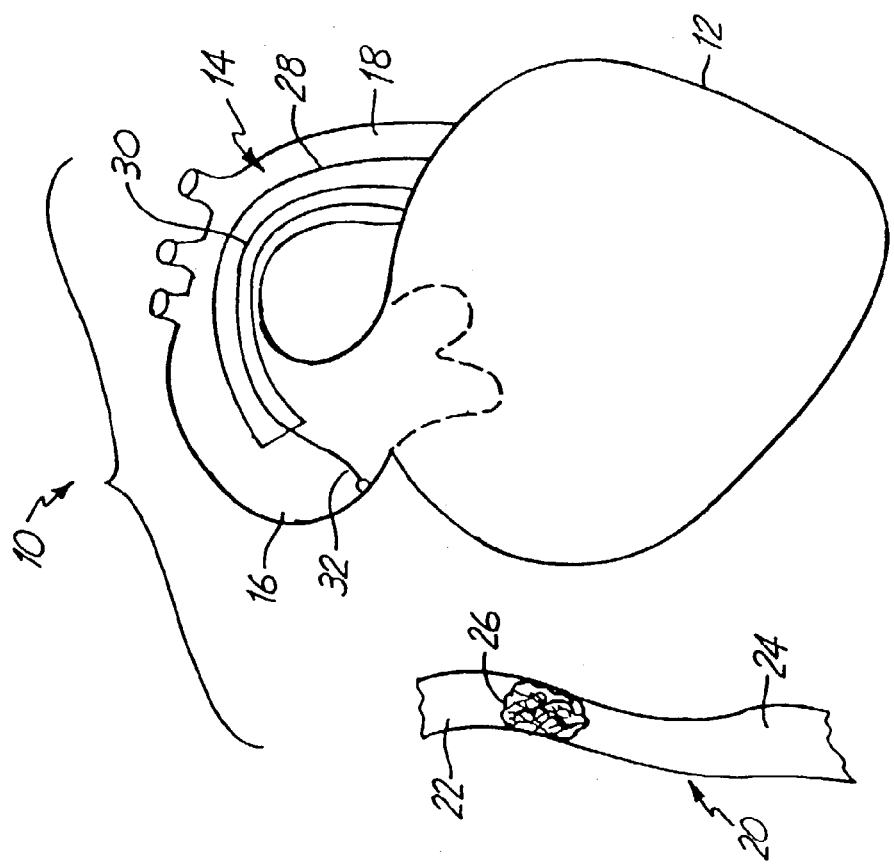

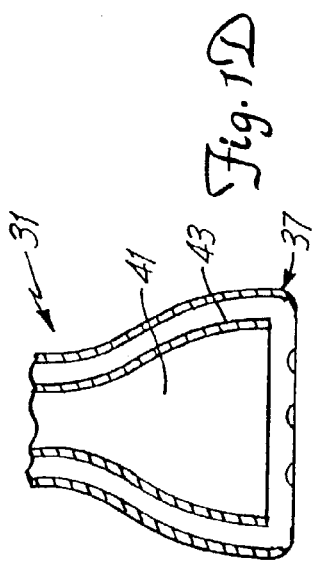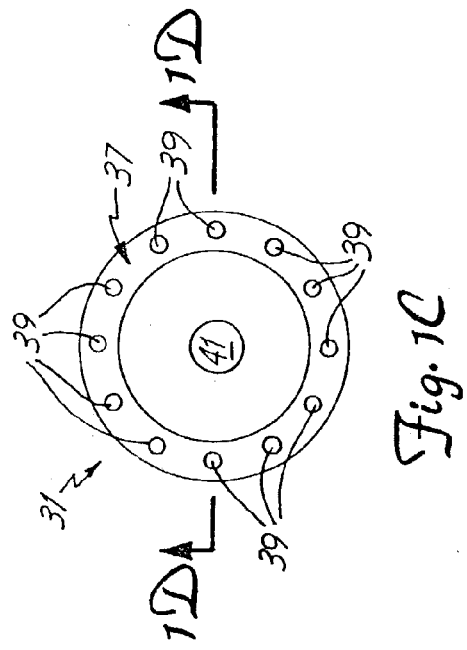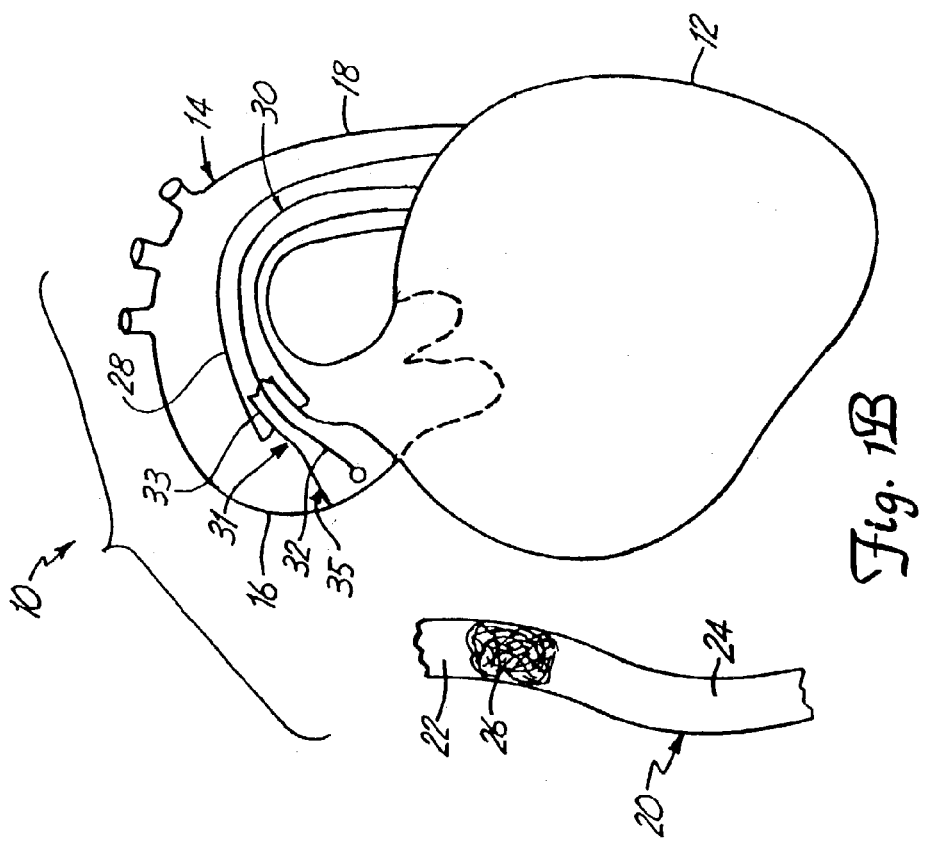

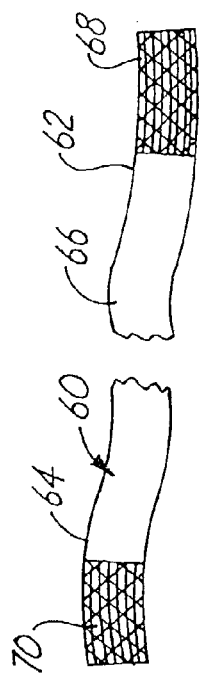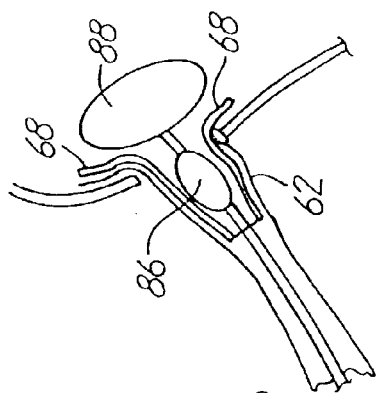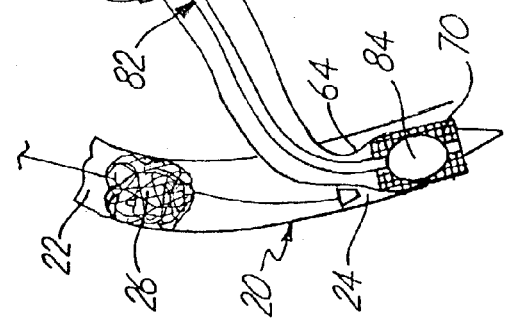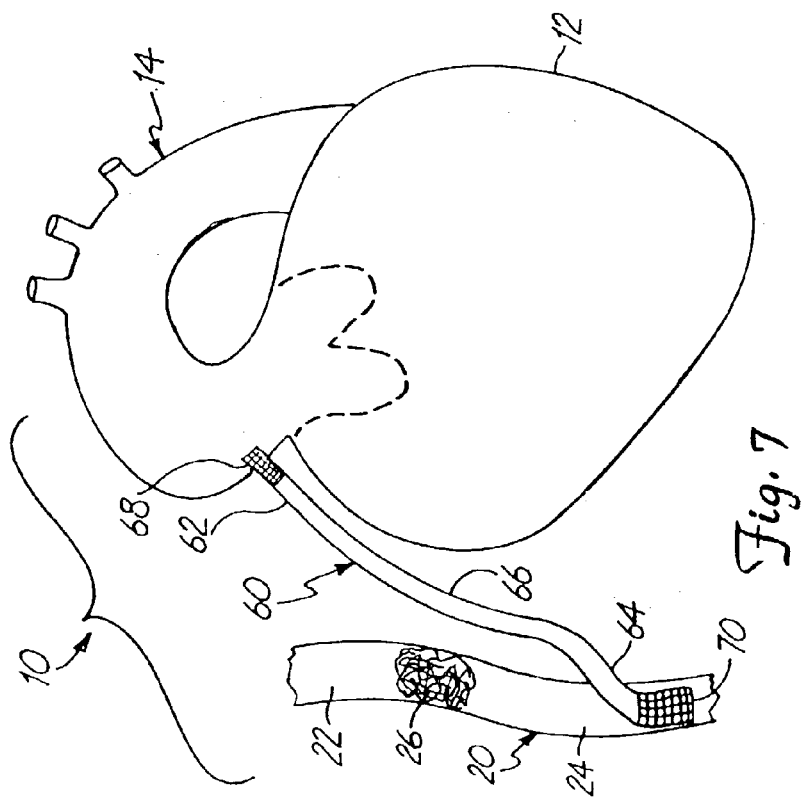
Fig. 8
Fig. 9
Fig. 7

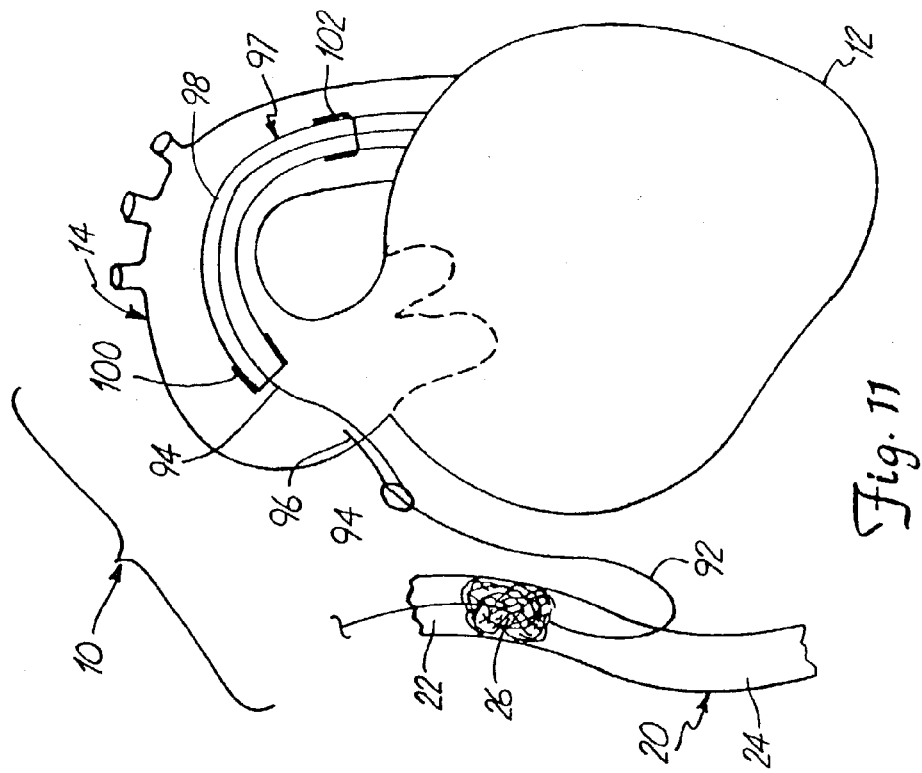
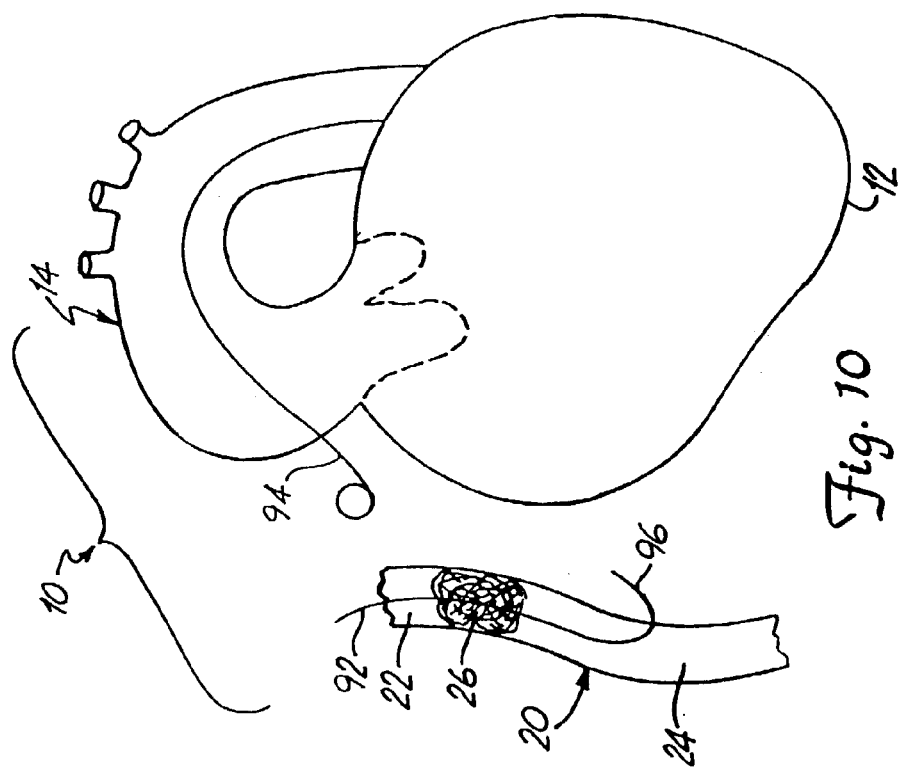

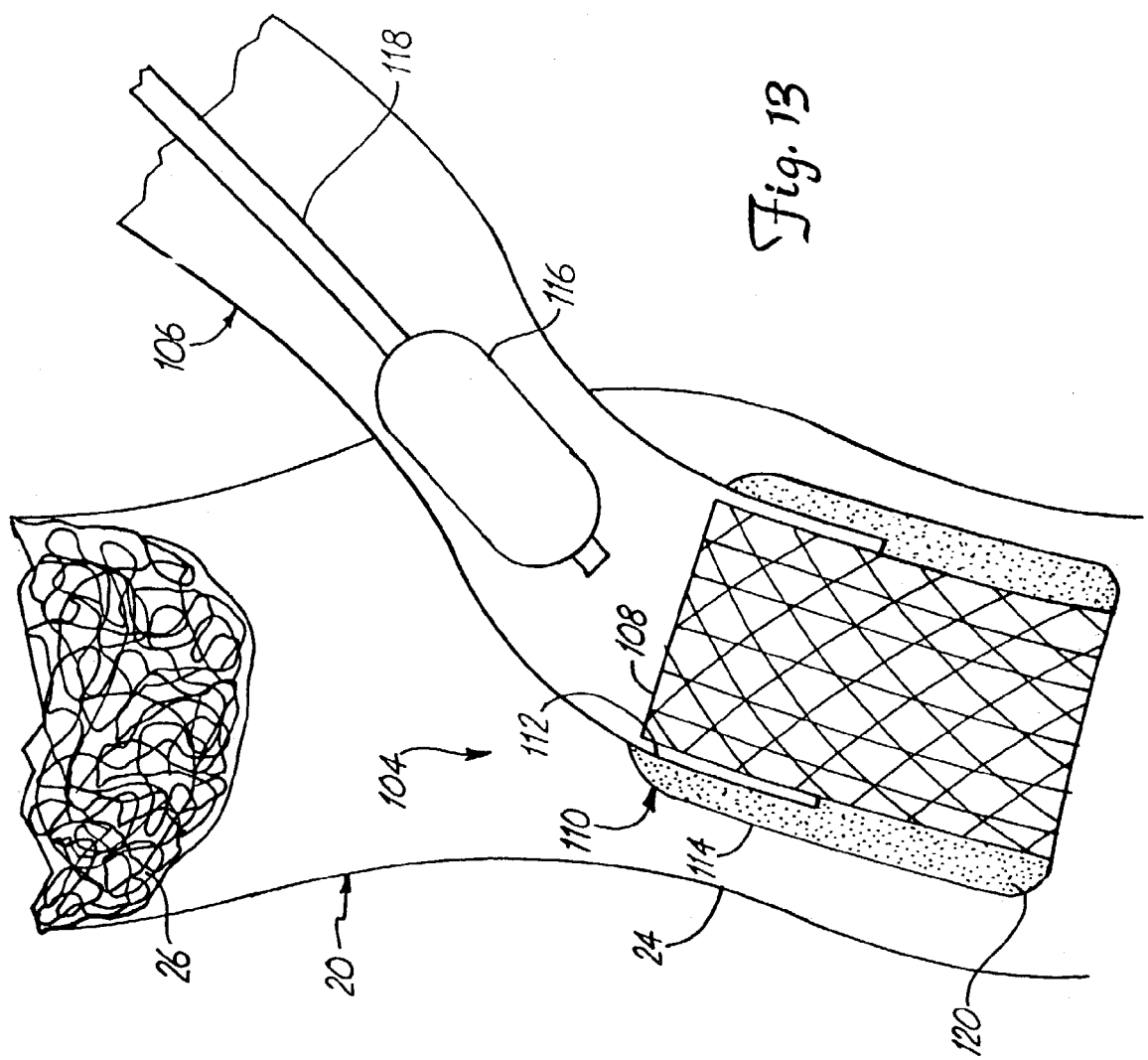

SYSTEM AND METHOD FOR PERCUTANEOUS CORONARY ARTERY BYPASS

CROSS-REFERENCE TO CO-PENDING APPLICATIONS

This application is a continuation of U.S. patent application Ser. No. 09/759,996, filed Jan. 12, 2001 now U.S. Pat. No. 6,575,168; which is a continuation of U.S. patent application Ser. No. 09/391,112, filed Sep. 7, 1999, now U.S. Pat. No. 6,253,769; which is a divisional of U.S. patent application Ser. No. 08/813,038, filed Mar. 6, 1997, now U.S. Pat. No. 6,026,814.

The following U.S. patent applications are hereby fully incorporated: U.S. patent application Ser. No. 08/813,040, entitled PERCUTANEOUS BYPASS WITH BRANCHING VESSEL, filed Mar. 6, 1997, now U.S. Pat. No. 6,035,856 and assigned to the same assignee as the present application; and U.S. patent application Ser. No. 08/812,879, entitled PERCUTANEOUS BYPASS BY TUNNELING THROUGH VESSEL WALL, filed Mar. 6, 1997, now U.S. Pat. No. 6,155,264 and assigned to the same assignee as the present invention.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are to diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped) or heart port (where the heart is stopped). Such a system which is used to perform a bypass is disclosed in the Sterman et al. U.S. Pat. No. 5,452,733.

SUMMARY OF THE INVENTION

A percutaneous system for bypassing a restriction in a native vessel of a mammal having an aorta includes providing a graft having a body portion with a first end, a second end and a lumen therebetween. An aperture is formed in the aorta. The graft is inserted into the aorta and the first end of the graft is connected to the aorta about the aperture in the aorta. An aperture is then formed in the native vessel distal of the restriction. The second end of the graft is connected to the native vessel about the aperture therein such that the lumen in the graft communicates with the aorta and the native vessel.

BRIEF DESCRIPTION OF THE DRAWINGS

FIGS. 1A–5 illustrate a system and method of percutaneously performing a coronary artery bypass procedure in accordance with one aspect of the present invention.

FIGS. 7–9F illustrate a system and method of deploying a coronary artery bypass using stents in accordance with the present invention.

FIGS. 10–12 illustrate a system and method used in performing a coronary artery bypass in accordance with another aspect of the present invention.

FIGS. 13 and 14 illustrate a system and method for forming an anastomosis in a coronary artery bypass procedure in accordance with the present invention.

DETAILED DESCRIPTION OF THE PREFERRED EMBODIMENTS

Figure 4:
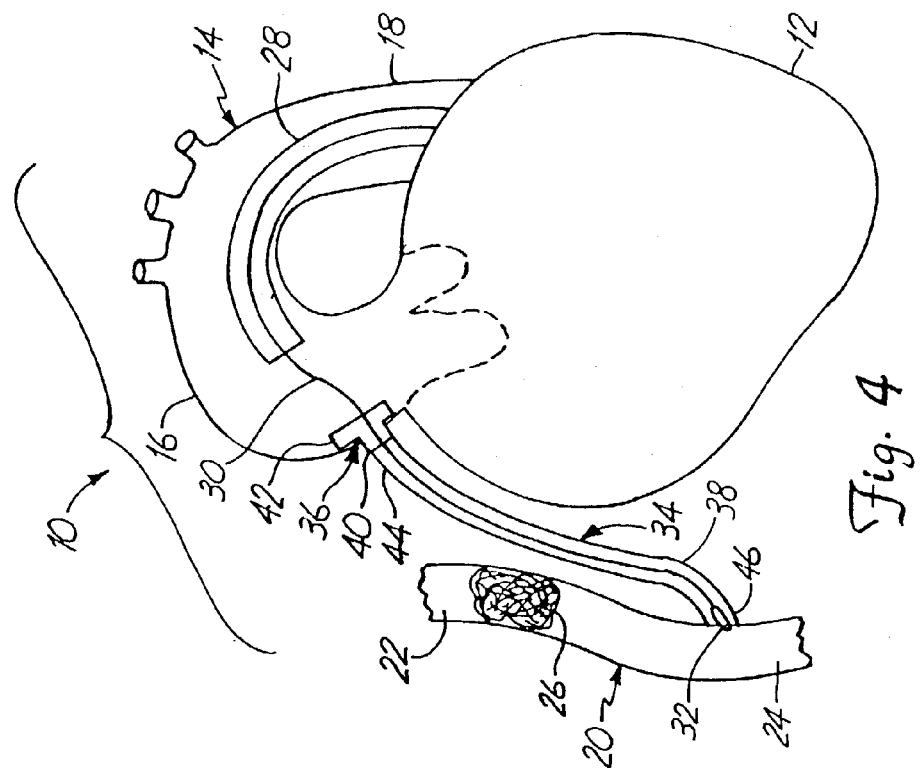

FIG. 1A illustrates a portion of vascular system 10. Vascular system 10 includes heart 12, aorta 14 (which includes ascending aorta 16 and descending aorta 18) and a restricted artery such as a coronary artery (native vessel) 20, only a portion of which is shown in FIG. 1A. Native vessel 20 is shown having a proximal portion 22 and a distal portion 24 with a partial or total restriction 26 (illustrated in FIG. 1A as an occlusion) therebetween. In accordance with one aspect of the present invention, occlusion 26 is bypassed in native vessel 20 by forming an aperture in aorta 14 and in native vessel 16. A graft is placed between the two apertures and an anastomosis is formed in the aorta and in native vessel 20 such that the graft communicates with the aorta and with the distal portion 24 of native vessel 20 (distal of occlusion 26).

Guide catheter 28 is first placed in aorta 14. In the preferred embodiment, guide catheter 28 enters the vasculature through a femoral artery and is passed through the vasculature, through descending aorta 18 and into a region proximate ascending aorta 16. Then, a cutting or boring device 30 is inserted through guide catheter 28. In the preferred embodiment, cutting device 30 is a guidewire or catheter having a cutting edge or cutting tip disposed at the distal end 32 thereof. Cutting device 30 is advanced through guide catheter 28 and out the distal end of guide catheter 28 and brought into contact with a portion of aorta 14 where an aperture is to be formed. Cutting device 30 is used to make an incision in the wall of the aorta.

While FIG. 1A illustrates cutting device 30 forming an incision in the right side of ascending aorta 16, the present invention contemplates forming an incision on any side of any portion of aorta 14. It is preferred that, when treating a diseased vessel on the right side of aorta 14, cutting device 30 forms an incision on the right side of aorta 14, and when treating a diseased vessel on the left side of aorta 14, cutting device 30 forms the incision on the left side of aorta 14. Also, while native vessel 20 is referred to herein as a coronary artery, the present invention can be used to treat substantially any diseased vessel 20.

In one embodiment, prior to making an incision in the wall of aorta 14, if the heart is stopped in order to prevent bleeding from the aorta after the incision is made. If the heart is stopped, it is preferably stopped using a known thoracic approach.

However, in the preferred embodiment, the heart is not stopped. Rather, blood flow through the incision in aorta 14 is prevented by other means. FIG. 1B illustrates one embodiment of a system for isolating the wall region of aorta 14 where the incision-is made.

Prior to making the incision in the wall of aorta 14 (either before or after cutting device 30 is advanced to the wall of aorta 14) isolation device 31 is advanced through aorta 14 to the wall region of the aorta where the incision is to be made. In one preferred embodiment, isolation device 31 is advanced through guide catheter 28. In the preferred embodiment, the tubular portion 33 of isolation device 31 extends proximally through guide catheter 28 to a vacuum pump or other device suitable for drawing a vacuum therethrough. Isolation device 31 preferably includes a catheter or tubular portion 33, a portion of which is shown in FIG. 1B.

Isolation device 31 also includes a distal end 35 which is placed in abutting arrangement with the wall region of aorta 14 where the incision is to be made.

In operation, after the distal end 35 of isolation device 31 is advanced to be adjacent the wall of aorta 14, the suction or vacuum device is actuated which pulls a vacuum through catheter portion 33 of isolation device 31 causing a vacuum to be created at the distal end 35 of isolation device 31. This causes a suction to occur in the distal end of isolation device 31 which draws the distal end 35 of isolation device 31 against the wall of aorta 14. This also removes blood from the region of the wall of the aorta where the incision is to be made and precludes additional blood flow from entering that area. Thus, a clear working space is created adjacent the wall of aorta 14 such that the incision can be made without a substantial amount of blood being released from the aorta 14 through the incision.

FIG. 1C is an end view of isolation device 31 taken from the distal end 35 of isolation device 31. FIG. 1C illustrates that distal end 35 of device 31 includes a radially expandable cone structure with a flexible ring 37 expandable and deployable therein. Ring 37 is preferably formed of a suitable polymer or other material which has a plurality of apertures 39 formed therein. Apertures 39 are connected through an interior lumen (shown in greater detail in FIG. 1B) to the proximal suction or vacuum device. When a vacuum is pulled through apertures 39, suction is formed between ring 37 and the wall of aorta 14 to hold ring 37 adjacent, and abutting against, the wall of aorta 14. FIG. 1C also illustrates that device 31 has an inner lumen 41 therethrough. In the preferred embodiment, once the clear working area adjacent the wall of aorta 14 is established, the cutting device 30 (and any other devices used in the procedure in accordance with the present invention) are advanced through lumen 41 as required.

FIG. 1D is a cross-sectional view of device 31 taken along section lines 1D—1D as shown in FIG. 1C. FIG. 1D illustrates that, in the preferred embodiment, isolation device 31 has an annular lumen 43 which extends proximally to the suction or vacuum device, and also communicates with the interior of flexible, expandable ring 37. The remainder of the present description proceeds with isolation device 31 removed from the figures, for the sake of clarity.

In another preferred embodiment, a low pressure vacuum is pulled through a guide catheter which has a flared distal end and a seal on a proximal end thereof. The sealed proximal end is preferably of the type which allows devices to be inserted therethrough while substantially maintaining a low pressure vacuum seal. Thus, the guide catheter forms a substantially sealed chamber in which the work is performed. It should also be noted that any other suitable isolation device can be used to prevent blood from flowing out of aorta 14 through the incision in the wall of aorta 14.

FIG. 2 is similar to FIG. 1, and similar items are similarly numbered. However, FIG. 2 shows that graft assembly 34 has been advanced to the distal end of guide catheter 28, and proximate the distal end 32 of cutting device 30. In one preferred embodiment, graft assembly 34 tracks over cutting device 30. However, graft assembly 34 can also move within cutting device 30 where cutting device 30 is a cutting catheter. Graft assembly 34 can also move adjacent cutting device 30 within guide catheter 28.

In any case, and in one preferred embodiment, graft assembly 34 includes coupler 36 and graft section 38. Coupler 36 is preferably a biologically compatible coupling device which has an insertion portion 40 and an annular shoulder 42. In the preferred embodiment, graft section 38 is preferably either a biologically compatible, artificial graft material (such as PTFE material), or a section of a human vein, such as a saphenous vein graft. Graft section 38 preferably has a first end 44 and a second end 46 with an inner lumen defined therebetween. Upon being inserted, graft section 38 is preferably inverted, or inside out, such that the normal inner lumen wall forms the outer wall of the graft section, while the normal outer wall forms the inner lumen wall of the graft section.

Figure 3:
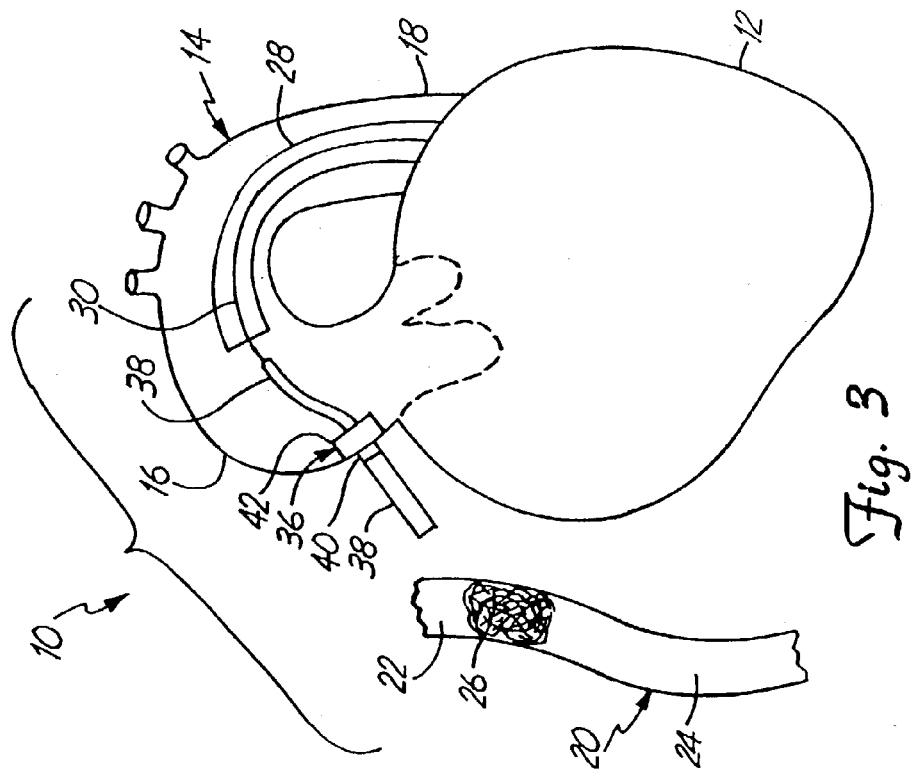

FIG. 3 illustrates graft section 38 being deployed between aorta 14 and native vessel 20. First, coupler 36 is placed in the aperture formed by cutting device 30 such that insertion portion 40 is inserted into the aperture and annular column 42 abuts, and rests against, an interior surface of the aortic wall. The first end 44 of graft section 38 remains connected to coupler 38. Graft section 38 is then pushed through coupler 36 until it comes out of the opposite end of coupler 36. In this way, graft section 38 turns inside out to become non-inverted. FIG. 3 illustrates that graft section 38 is advanced through coupler 36 until substantially the entire graft section is outside aorta 14 in a non-inverted position.

FIG. 4 illustrates graft section 38 after it has been completely advanced through coupler 36 and is in a non-inverted position. Coupler 36 is shown seated within the aperture formed in aorta 14. FIG. 4 also shows the next step in bypassing occlusion 26. First, end 46 of graft section 38 is moved to a spot adjacent the outer wall of native vessel 20 distal of occlusion 26. This spot can be located in any number of ways which will be described in greater detail later in the specification. End 46 of graft section 38 can be moved in the interstitial spaces between heart 12 and native vessel 20 also in a number of suitable ways, such as placing a guidewire therethrough with a maneuverable tip, or under the guidance of cutting device 30. In any case, once graft section 38 is located proximate native vessel 20 distal of occlusion 26, cutting device 30 is advanced through the lumen of graft section 38 to the portion of native vessel 20 distal of occlusion 26. Then, an aperture is formed in native vessel 20 through the use of cutting device 30. In a preferred embodiment, blood flow through native vessel 20 is completely occluded prior to making an incision therein. This can be done using occlusion balloons such as set out in the patent applications incorporated herein above, or using other suitable techniques.

Figure 5:
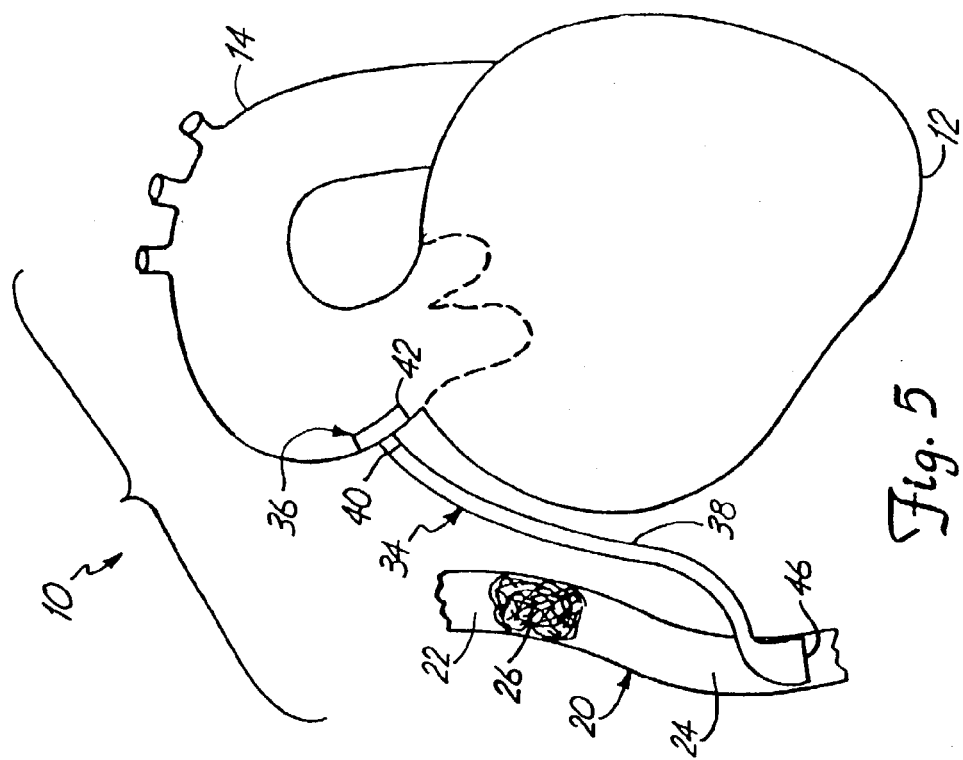

After the aperture is formed in the wall of native vessel 20, end 46 of graft section 38 is connected to native vessel 20 proximate the aperture. In one preferred embodiment, end 46 is sutured to native vessel 20 using an intraluminal suturing catheter. Intraluminal suturing devices are described in greater detail in the following U.S. Pat. No. 5,080,663 entitled SEWING DEVICE; U.S. Pat. No. 5,364,389 entitled METHOD AND APPARATUS FOR SEALING AND/OR GRASPING LUMINAL TISSUE; U.S. Pat. No. 5,545,171 entitled ANASTOMOSIS CATHETER; and U.S. Pat. No. 5,591,179 entitled ANASTOMOSIS SUTURING DEVICE AND METHOD and, which are hereby incorporated by reference. In another preferred embodiment, end 46 is advanced through the aperture in native vessel 20 and is placed in the distal portion 24 of native vessel 20. This is illustrated in FIG. 5. An anastomosis is then formed such that end 46 of graft section 38 is connected within distal section 24 of native vessel 20. The anastomosis can be formed in any suitable manner, such as with the placement of a stent, suitable adhesive, including biological adhesives, the application of growth factors, or other suitable anastomosis techniques. In this way, blood flows through aorta 14, in through coupler 36, through graft section 38, and to the portion of native vessel 20 distal of occlusion 26. Occlusion 26 is thus bypassed. The end 46 of graft section 38 in the distal portion 24 of native vessel 20 and coupler 36 eventually become permanently coupled within the vessels in which they are seated.

Figure 6A:
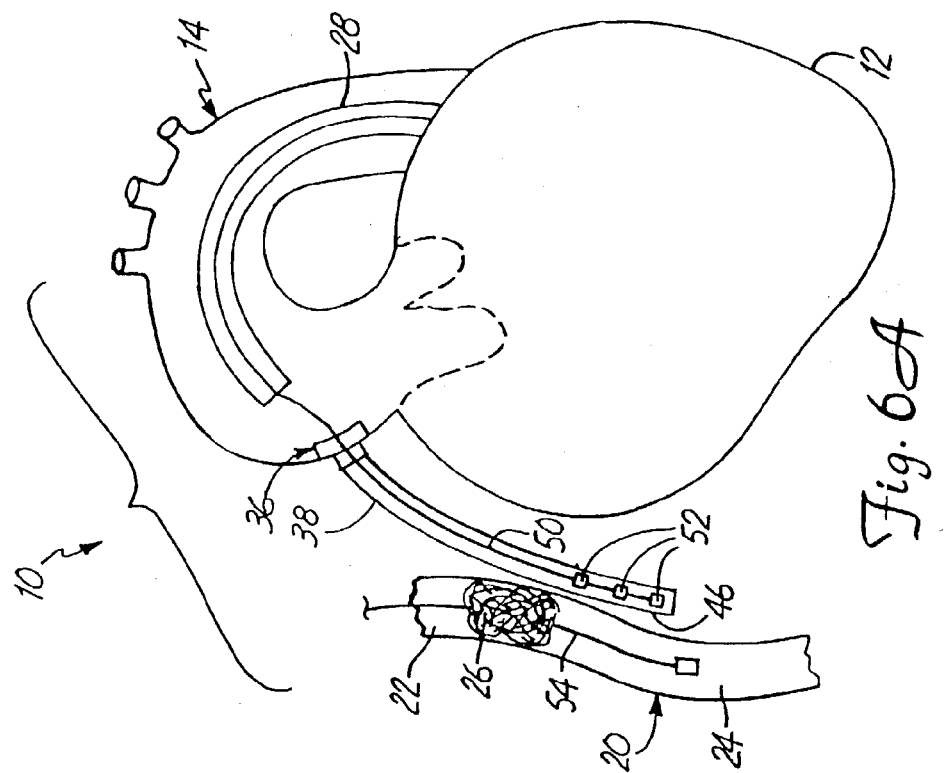
FIG. 6A illustrates a system for locating an anastomosis site in a native artery in accordance with another aspect of the present invention.
Figure 6B:
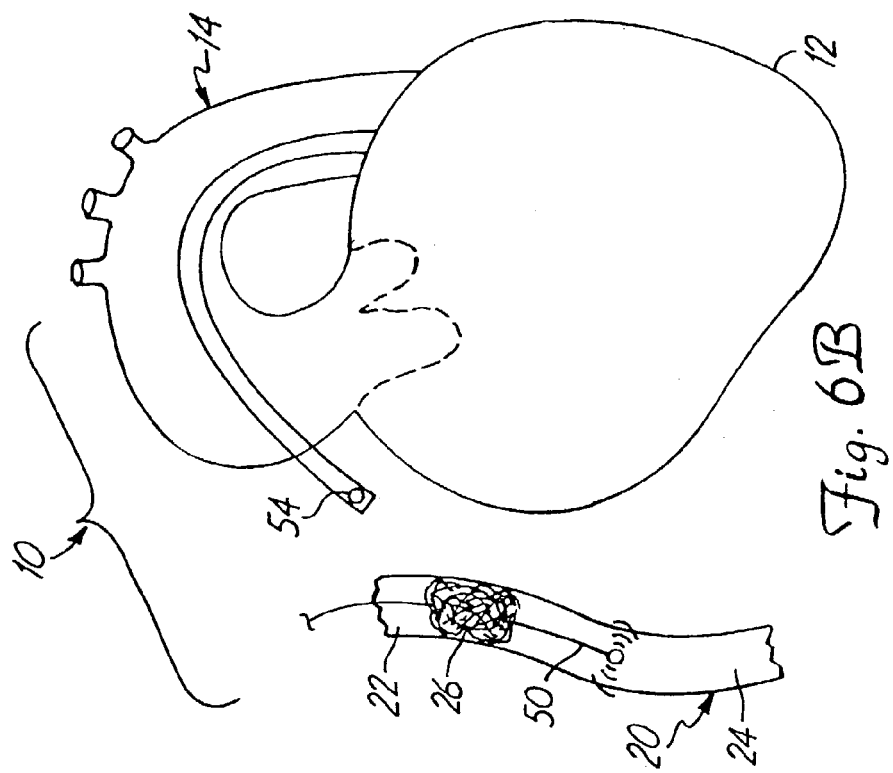
FIG. 6B illustrates a system for locating an anastomosis site in a native artery in accordance with another aspect of the present invention.

FIGS. 6A and 6B illustrate two embodiments in which the region 24 distal of occlusion 26 in native vessel 20 is located such that the aperture can be formed in distal section 24 and such that end 46 of graft section 38 can be placed appropriately.

In FIG. 6A, graft section 38 is shown having a positioning device 50 therein. In the embodiment shown in FIG. 6A, positioning device 50 includes an array of active transmitters 52 coupled to a convective wire or fiber. In the preferred embodiment, active transmitters 52 include ultrasound transmitters, radio frequency transmitters, a plurality of point light sources, or a single intense point light source, or an electro-magnetic transmitter (such as where current is selectively applied to a coil to induce a magnetic field thereabout). FIG. 6A also includes receiver device 54 which is located in parent vessel 20. Receiver device 54 is preferably compatible with transmitter array 52 so that it can receive the signals provided by transmitter array 52.

For instance, where transmitters 52 include an inductive magnetic coil, receiver device 54 includes a magnetic sensor array to receive the signals induced in the coil. Where transmitter array 52 includes an ultrasound transmitter, receiver 54 includes an ultrasound imager so that the relative positioning of receiver device 54 and transmitter array 52 can be determined. Where transmitter 52 includes a single point light source, or an array of point light sources, receiver device 54 includes a photodiode array or an imaging fiber optic bundle which can detect the light emitted by the light sources. In addition, where transmitters 52 include an RF transmitter, receiver device 54 includes a directional antenna. In any of the above cases, or similar cases, the relative position between transmitters 52 and receiver 54 can be determined so that end 46 of graft section 38 can be properly located adjacent parent vessel 20 relative to stenosis 26.

FIG. 6B is similar to FIG 6A except that receiver device 54 (or detector 54) and transmitter device 50 are switched such that the receiver device 54 is located in the graft section 38, while the transmitter device 50 is located in the native vessel 2C. The location system is operated similarly to that described with respect to FIG. 6A, and the relative position of the native vessel 20 and the tip of the graft section 38 are determined.

Alternatively, of course, graft section 38, or a wire inserted therethrough can have radiopaque markers on the distal ends thereof. In addition, a radiopaque marker can be inserted within vessel 20 distal of restriction 26. In that embodiment, bi-plane fluoroscopy is used for three dimensional localization in order to bring radiopaque markers located in vessel 20 and either in graft 38 or on the distal end of graft 38 together.

FIGS. 7–9F illustrate another aspect in accordance with the present invention. Similar items to those shown in the earlier figures are similarly numbered. However, system 10 shown in FIGS. 7–9F include a graft assembly 60 which has first end 62, second end 64, and graft body portion 66 which extends between ends 62 and 64 and defines a lumen therebetween. FIG. 7 illustrates graft assembly 60 deployed between aorta 14 and native vessel 20. First end 62 includes an expandable stent 68 for anchoring first end 62 within aorta 14. Second end 64 also includes an expandable stent 70 for use in anchoring second end 64 within native vessel 20.

FIG. 8 illustrates graft assembly 60 in greater detail. FIG. 8 shows that, in the preferred embodiment, stents 68 and 70 are formed of an expandable, woven, braided or mesh material which can be selectively expanded to have a preselected outer diameter which approximates the inner diameter of the vessel or aperture within which it is deployed. End 62 of graft body portion 68 is preferably attached to either the outer or inner surface of stent 68, and end 64 of graft assembly 60 is preferably attached to either the outer or inner surface of expandable stent 70. The connection between the stents and the graft body portion 66 can be accomplished in any number of suitable ways, such as through the use of an appropriate adhesive, such as weaving the stent directly into the graft material, such as by forming a frictional fit therebetween, or by utilizing another suitable connection mechanism.

FIGS. 9A–9F illustrate in greater detail the manner in which a graft assembly 60 is deployed within aorta 14 and in native vessel 20. First, a clear working area adjacent the wall of the aorta is isolated from blood flow in aorta 14. This can be done using, for instance, device 31 described earlier in the specification. Also, blood flow through vessel 20 is stopped.

Systems for stopping blood flow have included occluding balloons. Occluding balloons have a fairly low instance of emboli formation, and therefore have a fairly low instance of neurological problems which result from the formation of emboli.

Figure 9B:
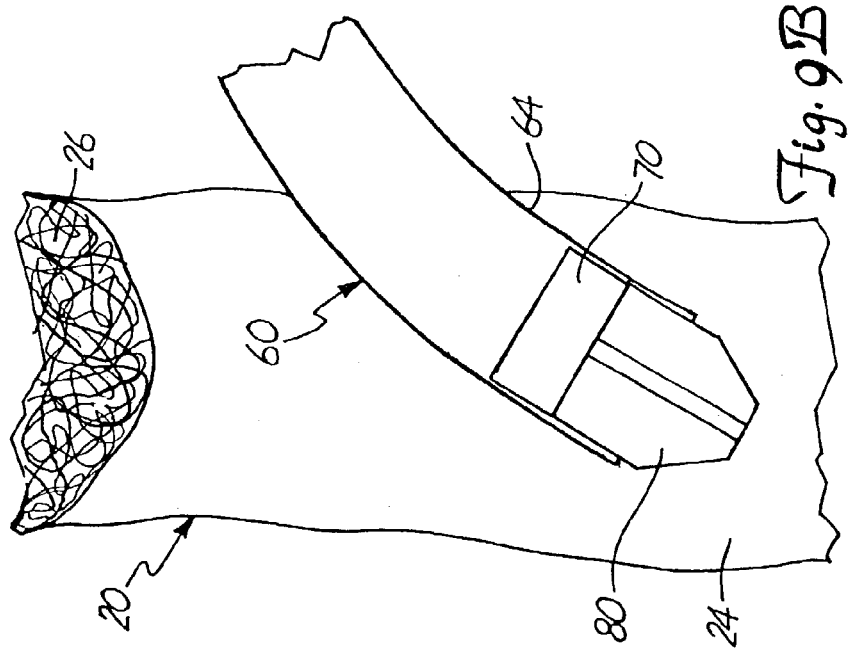
Figure 9A:
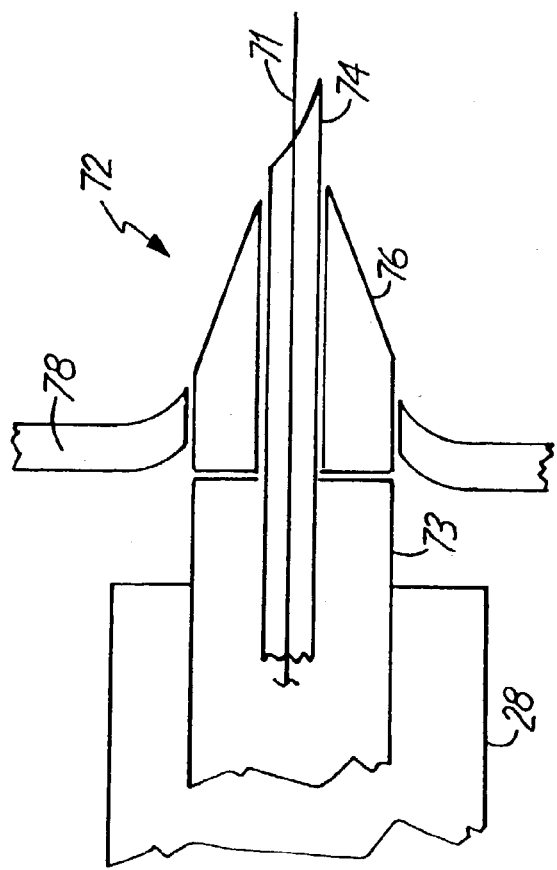

In any case, a guide catheter, such as guide catheter 28, is placed in aorta 14, and a quidewire 71 is advanced through the guide catheter. A cutting probe having the tip 72 shown in FIG. 9A is advanced-over the guidewire. Tip 72 includes a cutting needle 74 and a dialator sheath 76, and a catheter 73 is used to advance tip 72 over wire 71. In the preferred embodiment, needle 74 is used to make an incision in the wall 78 of aorta 14. Dialator 76 is then advanced through the incision 74. Catheter 73 is preferably a fully articulated, catheter with an ultrasonic tip, or with a fiber optic tip, or with another suitable means of observing the tip 72 during movement thereof.

In any case, tip 72 is moved adjacent native vessel 20. Needle 74 is then again advanced over wire 71 and native vessel 20 is pierced. Wire 71 is advanced into the native vessel 20 and contrast fluid is preferably injected to verify the position of tip 72 distal of occlusion 26 in native vessel 20. Wire 71 is held in place in the native vessel 20 as shown in FIG. 9B and the remainder of tip 72 is removed. An introducer tip 80 along with graft assembly 62, is then placed over wire 71. Introducer tip 80 is advanced through aortic wall 78 and through the aperture in native vessel 20 and carries with it graft assembly 62 to the position shown in FIG. 9B. Proper placement of stent 70 within native vessel 20 is verified through the injection of contrast medium.

A balloon catheter system, either inserted along with graft assembly 62, or after graft assembly 62 is located in the position shown in FIG. 9B, is then deployed. The balloon catheter system is shown in greater detail in FIG. 9C. Balloon catheter system 82 includes distal balloon 84, intermediate balloon 86, and proximal balloon 88. The balloons are spaced such that, when properly deployed, distal balloon 84 lies within stent 70, and proximal balloons 86 and 88 lie on the opposite side of the aortic wall 78, within stent 68. Alternatively, the different balloons can be independently movable and positioned relative to one another.

Figure 9C:
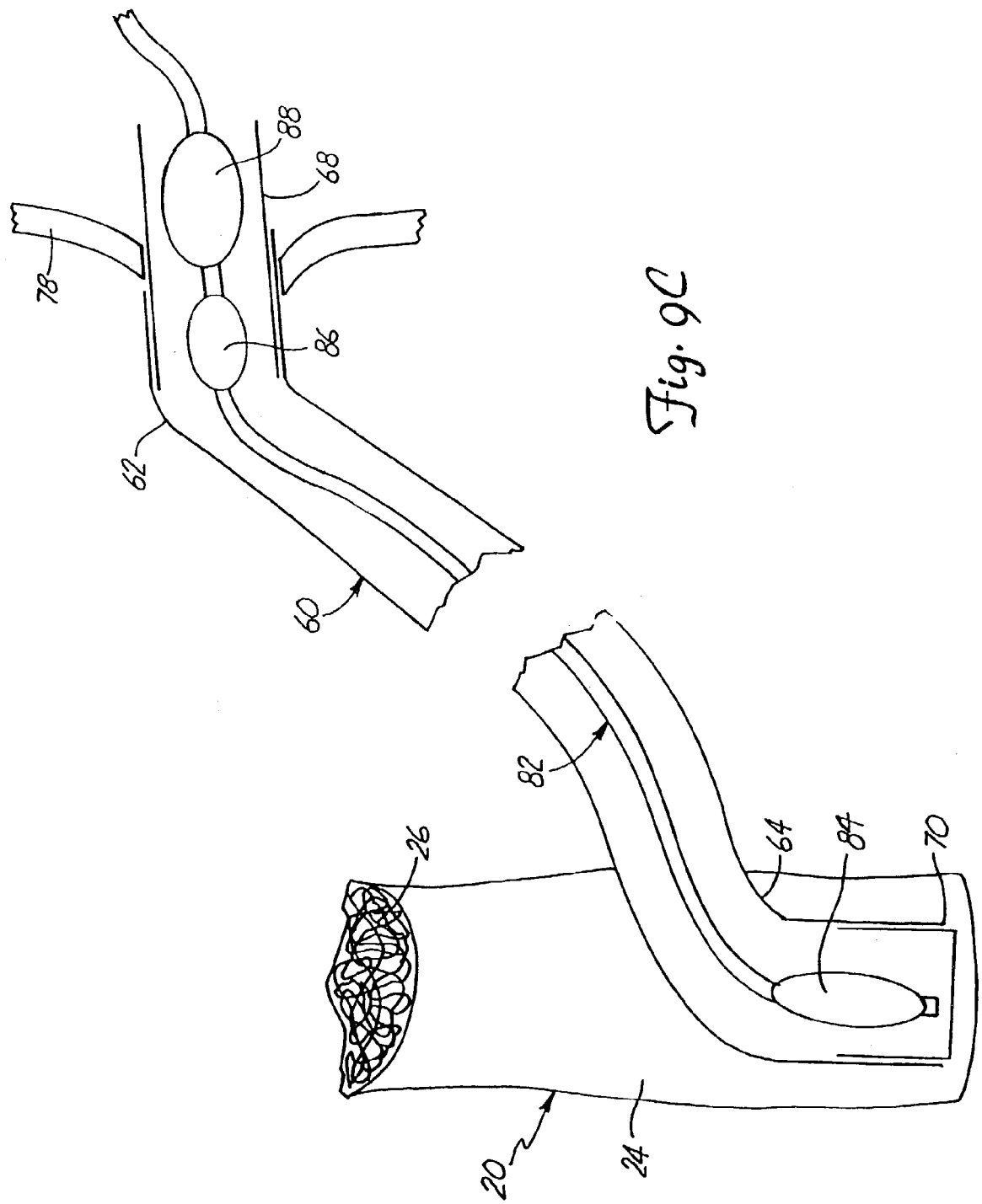

When balloon 84 is in place, within native vessel 21 and inside stent 70, it is inflated as shown in FIG. 9C. This causes stent 70 to expand to have an outer diameter which approximates the inner diameter of native vessel 20 and thus becomes anchored therein. Balloon 84 is then deflated, and introducer tip 80 is removed from the system.

Figure 9E:
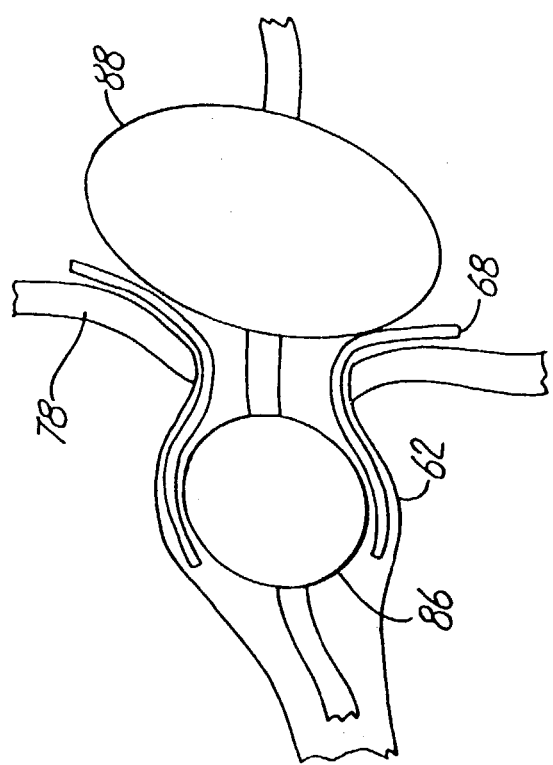
Figure 9D:
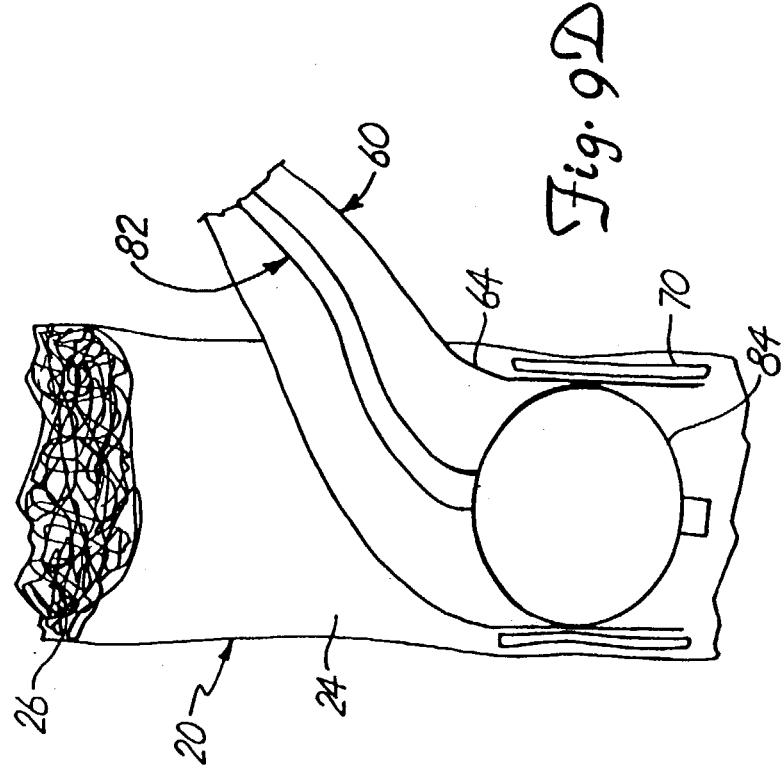

Intermediate balloon 86 is then inflated. This causes a distal section of stent 70 to expand, as shown in FIG. 9D, to have an outer dimension which is as large as, or slightly larger than, the incision formed in aortic wall 78. This prevents retrograde movement of stent 70 back into aorta 14. Balloon 88 is also inflated. As shown in FIG. 9E, balloon 88 is preferably relatively large so that is expands the proximal portion of stent 70 until it is deployed radially outwardly and substantially lies against the interior of aortic wall 78, in other words, the proximal portion of stent 70 mushrooms against the interior region of the aorta. In this way, balloons 86 and 88 deform stent 70 to inhibit substantial movement of stent 70 in the incision formed in the wall of the aorta.

Balloons 86 and 88 are then deflated and the core of the delivery system; including the catheter supporting balloons 86 and 88, and including wire 71, and any other portions of introducer tip 72, are removed. Such removal is facilitated by the deployment of the stents 68 and 70 which creates adequate clearance for removal of the remainder of the system. The injection of contrast medium is then used to verify that the bypass is not leaking, and the patient's heart (if it was stopped) is then restarted.

FIG. 9F shows deployment of stents 68 and 70 using balloons 84, 86 and 88, along with one preferred embodiment of a positioning device for use in positioning stent 70 in native vessel 20. The positioning device shown can preferably be any of the positioning devices already discussed, such as a point light source which is observed using a fiber optic bundle to accomplish placement of stent 70.

Figure 12:
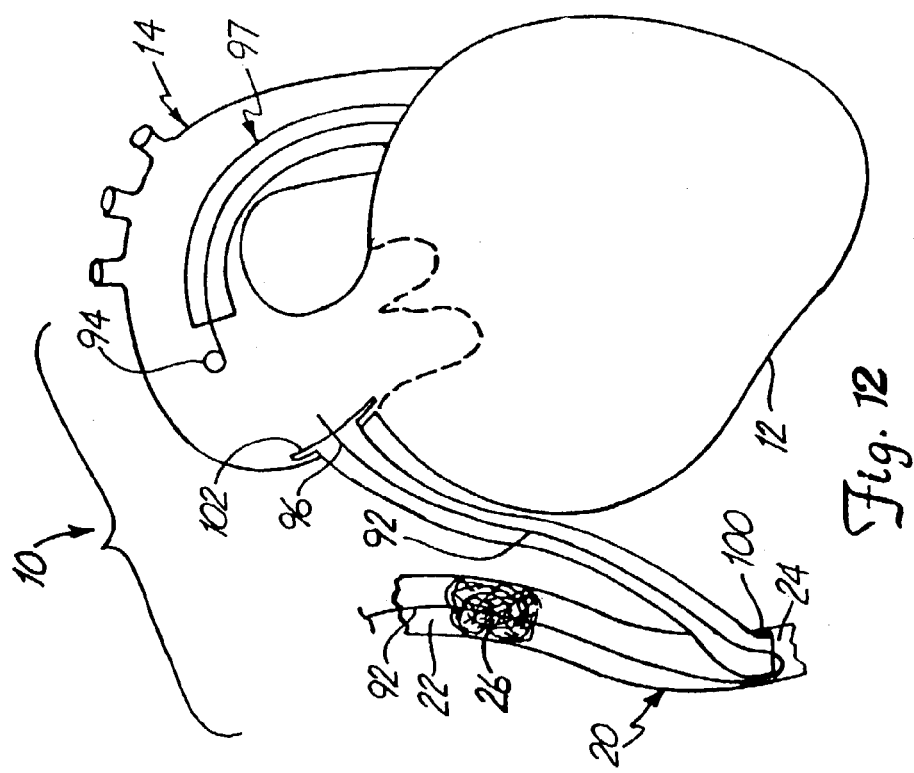

FIGS. 10–12 illustrate another aspect of the present invention. Similar items to those shown in earlier figures are similarly numbered. The system shown in FIG. 10 includes wire 92 and snare 94. In the preferred embodiment, distal tip 96 of wire 92 includes a cutting end, or another similar end, which can be used to cross occlusion 26. The distal tip 96 is thus moved distally of occlusion 26 and is used to pierce native vessel 20 distal of occlusion 26. Snare 94 is advanced through the vasculature percutaneously, to reside within aorta 14. This can be done using guide catheter 28 or other suitable advancement techniques. Snare 24, once positioned appropriately within aorta 14, is used to pierce the aorta and the distal tip of snare 94 is advanced through the aortic wall.

Then, as shown in FIG. 11, snare 94 is used to capture the distal tip 96 of wire 92. Distal tip 96 of wire 92 is then pulled back through the aperture in the aorta with snare 94 such that wire 92 extends all the way from within the distal portion 24 of native vessel 20, up through the aperture in aorta 14, and into the interior of aorta 14. Catheter 97, which preferably includes a removable tip portion 98, is advanced into the aorta over snare 94. In one preferred embodiment, the internal diameter of catheter 97 is approximately 0.035 inches. The detachable tip portion 98 of catheter 97 has a distal end 100 and a proximal end 102. Both ends 100 and 102 are preferably covered with a substance which enhances the formation of a tissue encapsulation thereover to provide an anastomosis. In one preferred embodiment, tips 100 and 102 are provided with a mesh thereover to encourage tissue growth thereon.

FIG. 12 shows that tip 98 is advanced over snare 94, and then wire 92, until end 100 resides within the inner lumen of native vessel 20, and so that end 102 resides within the aorta 14. Tips 100 and 102 can either be expanded such that they deploy radially outwardly and lies against the interior wall of the native vessel 20 and aorta 14, respectively, or they can simply extend inwardly into native vessel 20 and aorta 14. In any case, once the graft is properly placed, snare 94 is manipulated to release distal tip 96 of wire 92, and the snare 94 and wire 92 are removed leaving the graft in place.

Figure 14:
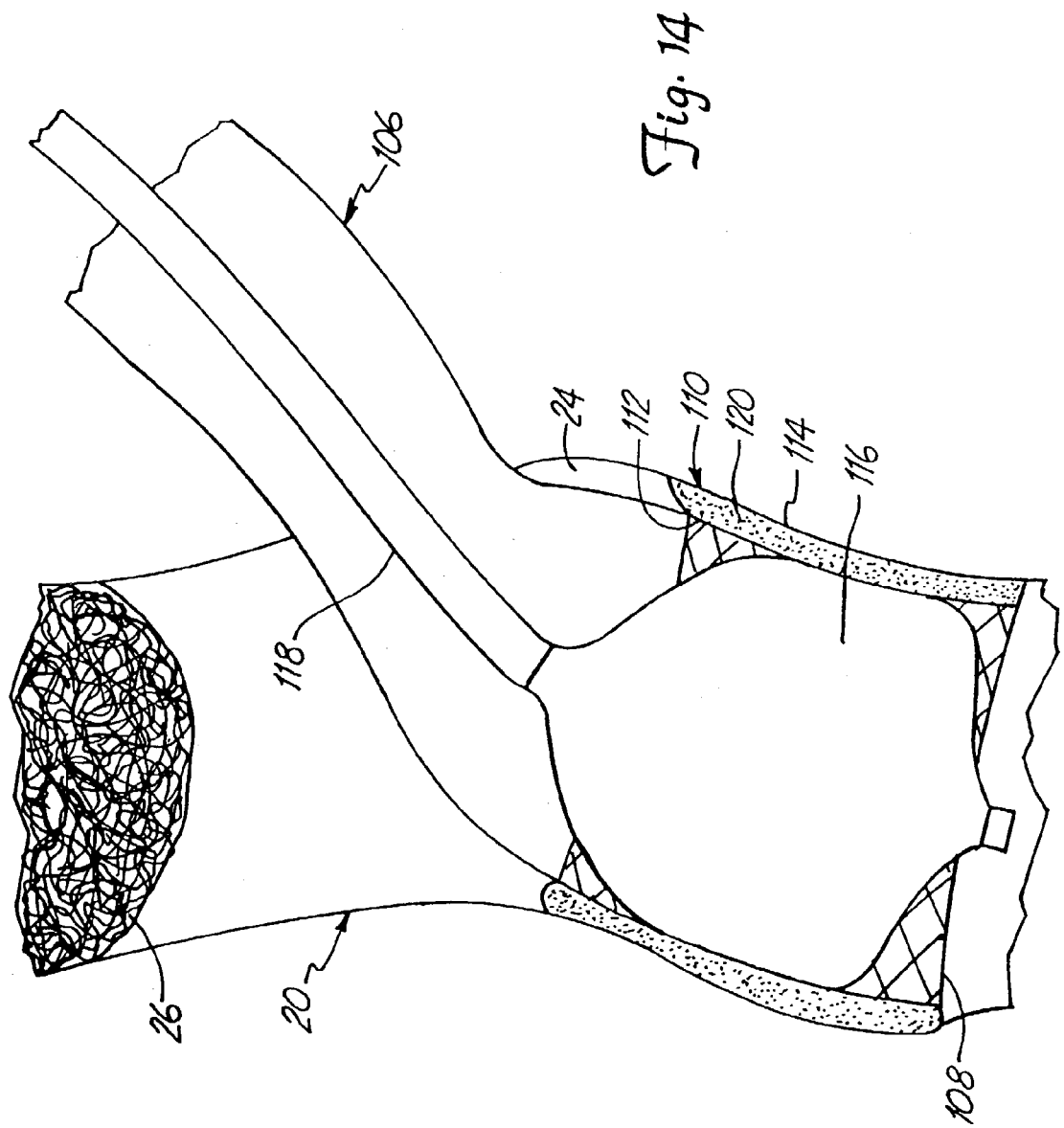

FIGS. 13 and 14 illustrate yet another aspect of the present invention. For the purposes of illustration of this aspect of the invention, a distal tip portion 104 of a graft 106 is shown deployed within distal portion 24 of native vessel 20. In the embodiment shown in FIGS. 13 and 14, tip 104 includes the distal region of either a man made graft, or a saphenous vein graft, or a similar graft section, along with a stent 108 located therein. Stent 108 can either be attached at its outer surface, or its inner surface, to the tip of graft 106.

In any case, the outer diameter of tip 104 preferably includes sheath 110. Sheath 110 preferably has an inner radial surface 112 which is impermeable to fluid flow, and an outer surface 114 which is semipermeable to fluid flow. Sheath 110 preferably includes a central portion 120 between inner surface 112 and outer surface 114 which contains either a substance suitable to enhance an anastomosis at that site, or another suitable drug. Once tip 104 is suitably located in distal region 24 of native vessel 20, inflatable balloon 116, supported by a balloon catheter 118, is inserted through graft 106 and into the interior of stent 108. Balloon 116 is then inflated to deploy stent 108 radially outwardly such that the outer diameter of tip 104 expands to a sufficient extent that it approximates the inner diameter of native vessel 20 and tightly fits therein.

Upon expansion of balloon 116, which is illustrated in FIG. 14, the outer surface 114 of sheath 110 is preferably rendered discontinuous (or broken) to release the substance carried by intermediate region 120 of sheath 110. In one preferred embodiment, the substance contained by region 120 of sheath 110 includes an adhesive which cures with the passage of time once stent 108 is deployed in vessel 20. This enhances anchoring of tip 104 within vessel 20. In another preferred embodiment, growth factors are contained within sheath 110 which also enhance an anastomosis in that region. In yet another embodiment, lesion-treating drugs are contained in sheath 110 such that, upon their release, they assist in dissolving, or otherwise treating, occlusion 26.

It should be noted that, in one preferred embodiment, extra working space can be created in the chest cavity in order to facilitate manipulation of the various devices described herein. According to one aspect of the present invention, a needle or cutting tip catheter is used to form an incision in the aorta as described above. Then, one of a number of things is used to create additional working space. For instance, a balloon may preferably be advanced through the hole in the aorta and expanded in the interstitial spaces proximate thereto to create additional working space. Also, bioabsorable, or removable, material can optionally be injected through the aperture in the aorta to expand the area thereabout and create additional working space. These features would preferably be used in order to replace $CO_2$ injection which is used in, for instance, laproscopic surgery.

Further, it should be noted that bifurcated stent grafts can be used in accordance with the present invention. Such grafts are described in greater detail in the patent applications incorporated herein by reference.

Thus, it can be seen that the present invention involves a system by which coronary artery bypass procedures can be executed substantially percutaneously. This serves to significantly reduce the disadvantages associated with prior treatment techniques.

Although the present invention has been described with reference to preferred embodiments, workers skilled in the art will recognize that changes may be made in form and detail without departing from the spirit and scope of the invention.

What is claimed is:

1. A method of bypassing a restriction in an artery of a mammal having an aorta, the method comprising:
   providing a graft having a body portion with a first end, a second end, and a lumen extending therebetween, wherein the graft includes a removable tip portion extending from a distal end of a catheter;
   forming an aperture in the aorta;
   inserting the graft into the aorta;
   connecting the first end of the graft to the aorta about the aperture in the aorta;
   advancing the body portion of the graft through the aperture in the aorta;
   forming an aperture in the artery distal of the restriction by advancing a wire across the restriction and forming the aperture in the artery with the wire;
   connecting the second end of the graft to the artery about the aperture therein such that the lumen in the graft communicates with the aorta and the artery; and
   detaching the graft from the distal end of the catheter.

2. The method of claim 1, further comprising:
   advancing a snare through the aperture in the aorta;
   capturing a distal end of the wire with the snare;
   moving the distal end of the wire into the aorta with the snare; and
   advancing the graft over the wire between the aorta and the artery.

3. A method of securing a graft to a vessel, the method comprising:
   providing a graft having a body portion with a first end, a second end and a lumen extending therebetween, wherein the graft includes a removable tip portion of a catheter;
   forming an aperture in the vessel;
   advancing a snare through the aperture in the vessel;
   advancing a wire across the restriction in the artery and forming an aperture distal of the restriction with the wire;
   capturing a distal end of the wire with the snare;
   moving the distal end of the wire into the vessel with the snare;
   advancing the graft over the wire between the vessel and the artery;
   connecting the first end of the graft to the vessel about the aperture in the vessel;
   connecting the second end of the graft to the artery about the aperture in the artery such that the lumen in the graft communicates with the vessel and the artery; and
   disconnecting the graft from the catheter.

4. A method of percutaneously attaching a graft to a vessel, the method comprising:
   providing a graft;
   forming a substantially round aperture in the vessel;
   providing a coupler comprising a first portion comprising an insertable portion securable to an end of the graft and a second portion comprising an annular shoulder securable to the vessel; and
   connecting the graft to the vessel by positioning the coupler proximate the aperture in the vessel;
   wherein the first portion of the coupler is secured to an inner surface of the graft and the second portion of the coupler is secured to an inner wall of the vessel.

5. The method of claim 4, wherein the second portion of the coupler has a diameter that is greater than a diameter of the aperture formed in the vessel.

* * * * *